US010808227B2

(12) United States Patent
Sawamura et al.

(10) Patent No.: US 10,808,227 B2
(45) Date of Patent: Oct. 20, 2020

(54) METHOD FOR PRODUCING PARVOVIRUS HAVING HIGH INFECTIVITY TITER AND HIGH PURITY

(71) Applicant: ASAHI KASEI MEDICAL CO., LTD., Tokyo (JP)

(72) Inventors: Yoshiyuki Sawamura, Tokyo (JP); Koichiro Yanagida, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 9 days.

(21) Appl. No.: 15/771,499

(22) PCT Filed: Oct. 5, 2016

(86) PCT No.: PCT/JP2016/079592

§ 371 (c)(1),
(2) Date: Apr. 27, 2018

(87) PCT Pub. No.: WO2017/077804

PCT Pub. Date: May 11, 2017

(65) Prior Publication Data

US 2018/0346883 A1 Dec. 6, 2018

(30) Foreign Application Priority Data

Nov. 6, 2015 (JP) ................................ 2015-218775

(51) Int. Cl.
*C12N 7/00* (2006.01)
*C12N 7/02* (2006.01)

(52) U.S. Cl.
CPC ................ *C12N 7/00* (2013.01); *C12N 7/02* (2013.01); *C12N 2750/14351* (2013.01)

(58) Field of Classification Search
None
See application file for complete search history.

(56) References Cited

U.S. PATENT DOCUMENTS

| | | | | |
|---|---|---|---|---|
| 4,904,468 A | 2/1990 | Gill et al. | | |
| 5,814,510 A | 9/1998 | Parrish et al. | | |
| 9,809,800 B2 * | 11/2017 | Yanagida | ................ | C12N 7/00 |
| 2009/0098159 A1 | 4/2009 | Mochizuki | | |
| 2012/0088228 A1 | 4/2012 | Asher et al. | | |
| 2015/0299668 A1 * | 10/2015 | Yanagida | ................ | C12N 7/00 435/239 |

FOREIGN PATENT DOCUMENTS

| | | | |
|---|---|---|---|
| GB | 1 401 565 | A | 7/1975 |
| JP | 58-22008 | B2 | 5/1983 |
| JP | 11-32757 | A | 2/1999 |
| WO | 99/07834 | A1 | 2/1999 |
| WO | 2011/130119 | A2 | 10/2011 |
| WO | 2014/080676 | A1 | 5/2014 |

OTHER PUBLICATIONS

Zhang et al. (Tropical Animal Health and Production. 2010; 42 (8): 1611-1613).*

Geletneky et al. (Comparative Medicine; Feb. 2015; 65 (1): 36-45).*

"Virus Saikin Kansen new File", edited by Yoshiyuki Nagai and Haruo Watanabe, Yodosha Co., Ltd., pp. 68, (1997).

"Virology", edited by Masakazu Hatanaka, Asakura Publishing Co., Ltd., pp. 222-223, (1997).

Azetaka et al., "Studies on Canine Parvovirus Isolation, Experimental Infection and Serologic Survey", Jpn. J. Vet. Sci., 43, pp. 243-255 (1981).

"Virus Jikkengaku Sohron", edited by Gakuyukai, The National Institute of Health, pp. 61, 113, 131, 166-177, (1973), with partial English translation.

Bachmann, "Porcine Parvovirus Infection In Vitro: A Study Model for the Replication of Parvoviruses—I. Replication at Different Temperatures", Proc. Soc. Exp. Biol. Med., vol. 140, pp. 1369-1374, (1972).

Bachmann et al., "Porcine Parvovirus Infection in vitro: A Study Model for the Replication of Parvoviruses—II. Kinetics of Virus and Antigen Production", Zbl. Vet. Med. B, 23, pp. 355-363, (1976).

"Virus Jikkengaku Kakuron", edited by Gakuyukai, the National Institute of Health, pp. 22-23, (1973), with partial English translation.

Slocum et al., "Impact of Virus Preparation Quality on Parvovirus Filter Performance", Biotechnology and Bioengineering, vol. 110, No. 1, pp. 229-239, (published online Aug. 6, 2012).

International Search Report for PCT/JP2016/079592, dated Dec. 27, 2016, with English translation.

International Preliminary Report on Patentability for PCT/JP2016/079592, dated May 8, 2018.

Supplementary European Search Report for EP 16861871.8, dated Jul. 3, 2018.

* cited by examiner

*Primary Examiner* — Shanon A. Foley
(74) *Attorney, Agent, or Firm* — Greenblum & Bernstein, P.L.C.

(57) ABSTRACT

Provided are a parvovirus derived from an unconcentrated cell culture supernatant, having a infectivity titer of $10^9$ $TCID_{50}$/mL or more and an {infectivity titer ($TCID_{50}$/mL)}:{impurity protein concentration (ng/mL)} ratio more than 5000:1; and a method of producing such a high-infectivity titer and high-purity parvovirus.

9 Claims, No Drawings

METHOD FOR PRODUCING PARVOVIRUS HAVING HIGH INFECTIVITY TITER AND HIGH PURITY

TECHNICAL FIELD

The present invention relates to a method of producing a high-infectivity-titer and high-purity parvovirus in a culture supernatant, and a high-infectivity-titer and high-purity parvovirus obtained by the method.

BACKGROUND ART

Viruses infect many plants and animals including humans and also many microorganisms and amplify therein. Some are DNA viruses having DNA as a genome and some are RNA viruses having RNA as a genome. Each of these viruses has different amplification mechanism. Many viruses cause viral infection in animals such as humans when infecting them. Viruses cannot increase by themselves but can increase by infecting the cells of other animals, plants, or microorganisms and making use of the ability of their cells. Cells allowing the infection and growth of viruses therein are called "host cells" of these viruses. The kind of host cells allowing the infection and growth of viruses therein depends on the kind of the virus.

Parvovirus is a small single-stranded DNA virus. It is an icosahedral virus having a diameter as small as about 20 nm and does not have an envelope (Non-Patent Document 1). Parvovirus infects animals to cause a disease. The known disease caused the parvovirus includes infectious erythema as well as anemia, and arthritis that B19 parvovirus causes in humans, anemia due to simian parvovirus (SPV), cat enteritis, leucopenia, and dystonia due to feline parvovirus (FPV), dog enteritis and myocarditis due to canine parvovirus (CPV), pig stillbirth due to porcine parvovirus (PPV), cow enteritis due to bovine parvovirus (BPV), goose enteritis and myocarditis due to goose parvovirus (GPV), and mouse enteritis and hepatitis due to minute virus of mice (MVM) (Non-Patent Documents 2 and 3). Parvovirus is important as a pathogen causing diseases in animals such as dogs and cats kept by humans. It is known that dogs infected with canine parvovirus suffer from enteritis as described above, develop severe diarrhea and vomiting, and die (Non-Patent Document 3). Cats infected with parvovirus sometimes develop acute enteritis or leukopenia and have the possibility of dying from secondary infection. Fetuses or newborn infants of cats infected with the virus may be damaged in the central nerve or thymus to develop ataxia or die.

To prevent parvovirus infection, studies on vaccines against parvovirus have been conducted (Patent Documents 1 and 2). For these studies, production of a virus and use of the virus are inevitable. Many viruses can be grown and produced by culturing host cells and infecting them with the viruses. The production of a vaccine by attenuating or inactivating a virus is achieved by the procedure same as that of virus production.

In the pharmaceutical industry, it is necessary to evaluate virus clearance (removal performance) of the production process in order to assure that a pharmaceutical of biological origin, such as a recombinant pharmaceutical (a biopharmaceutical) or an antibody pharmaceutical, is not contaminated with virus (virus safety). The virus clearance which individual steps have is analyzed by adding the virus to an intermediate product of a pharmaceutical before each step and determining the amount of the virus before and after the step. Particularly, porcine parvovirus (PPV) which is a kind of parvovirus has been used with high frequency for the virus clearance evaluation of a plasma derivative performed by the method described in the ICH (International Conference on Harmonization of Technical Requirements for Registration of Pharmaceuticals for Human Use) guideline prescribed for the method of selecting the kind of a virus used for the virus clearance evaluation in biologics production processes. For the virus clearance evaluation of a biopharmaceutical, Minute virus of mice (MVM) which is a kind of parvovirus has been used with high frequency. Thus, parvovirus is used with high frequency for the virus clearance evaluation of biologics production processes.

A virus is produced by a method using: a laboratory animal; hen's eggs; and tissue culture or cultured cells (Non-Patent Document 4). The method using a laboratory animal or hen's eggs has the disadvantage of high cost. Instead of them, the method using cultured cells can be used. Parvovirus is also produced by the method using cultured cells (Patent Document 1).

For the production of a virus such as parvovirus, it is the common practice to infect a culture system of host cells with its seed virus and then, proliferate and collect the virus. The term "seed virus" as used herein is referred to a small amount of the virus used in the initial stage of virus growth, which is deemed as "seed". In the conventional virus production, host cells are infected with a seed virus usually at the time when the host cells reach confluence and form a monolayer state (Non-Patent Document 4, Patent Documents 3 to 6). More specifically, the seed virus is usually inoculated while the host cells inoculated into a culture vessel are proliferated to spread all over the bottom surface of the culture vessel, because a presence of a high density cells which can be infected with the virus is a system that provides a site for the production of a larger number of viruses. It usually takes two or three days from the inoculation of the host cells into the culture vessel until they reach a confluent state (Non-Patent Document 4). In this confluent state, the host cells are in a stationary phase and do not grow further. Thus, in the conventional technology, after completion of a growth culture step of host cells, virus infection is started under a culture environment where further cell growth does not occur and a virus is produced in a culture supernatant concurrently with the death of the host cells caused by the virus infection. Parvovirus is no exception and virus production is performed by a method of infecting confluent-state cells therewith (Non-patent Document 5 and Non-patent Document 6) and the infectivity titer of the parvovirus thus obtained was $10^5$ to $10^7$ $TCID_{50}$/mL. In the conventional culture system, parvovirus is added to host cells in a confluent state, that is, a state having the largest number of cells, and the parvovirus thus added grows in host cells and increases with the attendant death of the host cells. By collecting a supernatant at the time when the infectivity titer of parvovirus becomes the highest, a parvovirus solution having the highest infectivity titer can be collected. Needless to say, the parvovirus obtained in the culture supernatant by this method is collected as a suspension in the medium provided for the cell culture.

After the parvovirus solution is obtained as described above, impurities are removed from it. As a removal method, impurities such as cell debris are removed by low-speed centrifugal separation (Non-Patent Document 7).

CITATION LIST

Patent Documents

Patent Document 1: WO2007/125605
Patent Document 2: JP H 10-508485 T

Patent Document 3: JP 2009-297036 A
Patent Document 4: JP 2655876 B
Patent Document 5: JP S 58-22008 B
Patent Document 6: JPS 61-24370 A Non-Patent Documents Non-Patent Document 1: Virus•Saikin Kansen new File, 1997, edited by Yoshiyuki Nagai and Haruo Watanabe, Yodosha Co., Ltd., p. 68
Non-Patent Document 2: Virology, 1997, edited by Masakazu Hatanaka, Asakura Publishing Co., Ltd., p. 222-223
Non-Patent Document 3: M. Azetaka, et. al, 1980, Jpn. J. Vet. Sci. 43: 243-255
Non-Patent Document 4: Virus Jikkengaku Sohron edited by Gakuyukai, the National Institute of Health, 1973: 61, 113, 131, and 166-176
Non-Patent Document 5: P. A. Bachmann, 1972, Proc. Soc. Exp. Biol. Med. (140) 4: 1369-1374
Non-Patent Document 6: P. A. Bachmann et al., 1976, Zbl. Vet. Med. B., No. 23: 355-363
Non-Patent Document 7: Virus Jikkengaku Kakuron, 1973, edited by Gakuyukai, the National Institute of Health, p. 22-23.

SUMMARY

Technical Problem

As described above, there is a demand for the production of a high-infectivity-titer parvovirus for use in the virus safety evaluation of a pharmaceutical of biological origin or vaccine production.

Further, there is a demand for the production of a high-infectivity-titer virus also in the virus clearance evaluation of the production processes of biologics as described above. The virus clearance test of a virus removal filter for the evaluation is performed in a model step in which an actual production process is scaled down. What are required for this virus clearance test are: first, the virus suspension is added in an amount not causing clogging of a filter; and second, the addition amount is an amount to give a log reduction value (LRV) of 4 or more, wherein the value is a virus clearance value of a step to be evaluated. In the first case, the addition amount is required not to cause clogging by the virus addition because various parameters including the flow rate in the step should be equal to those of the actual production process (WHO Technical Report, Series No. 924, 2004 162-165). To achieve this, addition of 1% or less, preferably 0.1% or less in terms of a volume ratio is desired. For the second case, since a step having LRV of 4 or more is regarded as a robust, effective, and reliable process step for virus removal, the amount of the virus to be added is required to be an amount capable of giving LRV of 4 or more (WHO Technical Report, Series No. 924, 2004 163-164) as a result. Thus, LRV as virus removal performance is required to show 4 or more and the amount of the virus suspension to be added to an intermediate product is desirably 1% or less, preferably 0.1%, in terms of a volume ratio. However, it becomes difficult to give LRV of 4 or more due to problems such as loss in a prefilter or quantitative error when 1% or 0.1% of a low-infectivity-titer parvovirus obtained by a conventional culture method (infectivity titer: $10^5$ to $10^7$ $TCID_{50}$/mL,[{infectivity titer of parvovirus ($TCID_{50}$/mL)}:{impurity protein concentration (ng/mL)} ratio=(less than 10):1] is added. Here, to give an LRV of 4 or more without failure, the virus addition volume must be increased, which however is likely to cause negative effects such as clogging of the filter.

In recent years, a virus removal property when a viral load per unit membrane area is made greater than a conventional load has attracted attentions as new evaluation criteria of a virus removing membrane. In this evaluation, a larger amount of a virus solution than that of conventional measurement is filtered so that with an increase in the amount of a virus suspension to be added, a larger amount of an impurity protein contained in the virus suspension is filtered together, resulting in an increase in the possibility of occurrence of negative effects such as clogging of the filter. The impurity protein concentration contained in the virus solution is therefore desired to be lower further.

Conventionally, in order to overcome such a problem, it was possible to employ a method of concentrating a virus by carrying out ultracentrifugation and thereby precipitating it and the like method. Such methods however simultaneously concentrate an impurity, which may inevitably have an adverse effect of impurities on the experimental results or filtration through a virus removal filter.

In addition, a technique of concentrating a virus by density gradient ultracentrifugal separation such as cesium density gradient ultracentrifugation or sucrose density gradient ultracentrifugation is markedly cumbersome in operation and requires a difficult skilled technique. Further, the volume of a centrifuge tube of a general purpose ultracentrifuge is limited and this makes scale-up difficult so that the technique can generally be used only in a small-scale experiment and industrial use of such a concentration step is not practical.

There is also known a method of, in order to obtain a high-infectivity-titer virus suspension, collecting infected cells, repeating freezing and thawing to forcibly and physically destructing the resulting cells, and thereby collecting the virus accumulated inside the cells. This is a virus production method usually performed for minute virus of mice but this method inevitably causes mixing, in the virus, of a large amount of impurities in host cells.

Thus, it is extremely difficult to employ the conventional virus production technique. There is therefore a demand for a method of more conveniently and efficiently obtaining a high-purity and high-infectivity-titer parvovirus without using a concentrating operation such as ultracentrifugal separation requiring a complicated operation.

Solution to Problem

The present inventors found first that a parvovirus having an infectivity titer higher than that obtained by the conventional method was obtained by infecting host cells having a cell density within a markedly low specific range which had not been used conventionally with a seed virus of parvovirus at a low multiplicity of infection (MOI) within a specific range and culturing the host cells for a predetermined period of time, and collecting the culture supernatant and thereby making use of a growth mechanism typical of the parvovirus. (WO2014/080676)

Further, with a view to overcoming the above-described problem, the present inventors have carried out an intensive investigation on the relationship between various conditions (initial host cell density or culture time including medium replacement time) in a culture system of inoculating host cells with a seed virus of a parvovirus and proliferating the parvovirus and the infectivity titer and purity of the virus thus obtained. As a result, it has been found surprisingly that a parvovirus having an extremely high infectivity titer and high purity that has not been obtained by the conventional method can be obtained using a method not conventionally employed, that is, a method including determining the number of host cells at the time of infection by using a calculation method not conventionally used, culturing host cells for a predetermined period of time, replacing the culture supernatant with a serum-free medium once, and collecting the supernatant after additional culturing for a predetermined term.

Described specifically, the present invention is as described below.

[1] A method of producing a high-infectivity-titer and high-purity parvovirus, including:

(a) a step of preliminarily calculating, every 24 hours, a time-dependent change of a cell density in a culture substrate when host cells are infected with a parvovirus for each cell density (A) when infecting virus;

(b) a step of determining, based on the time-dependent change of a cell density calculated preliminarily in the step (a), (b1) time ($T_{max}$) from infection to peak time of the time-dependent change of a cell density, (b2) a cell density ($B_{max}$) at $T_{max}$ and $A_1$ which is A that satisfies the following equation (1), (b3) the maximum ($A_{max}$) of the cell density $A_1$ when infecting virus, and (b4) $A_2$ that satisfies the following equation (2), $$B_{max}/A1>1.2 \quad \text{Equation (1)}$$

$$A_{max} \geq A2 \geq A_{max}/10 \quad \text{Equation (2)}$$

(c) a step of inoculating a seed virus of a parvovirus into the culture substrate containing host cells having the cell density $A_2$ when infecting virus determined in (b4) of the step (b) and a serum medium to give a multiplicity of infection (MOI) of from 0.001 to 0.1;

(d) a step of culturing a cultured product containing the host cells and the parvovirus obtained in the step (c) for a time period of $T_{max}$ or more to less than ($T_{max}$+48) hours, wherein $T_{max}$ is determined in (b1) of the step (b);

(e) a step of replacing a culture supernatant obtained in the step (d) with a serum-free medium and culturing for 12 hours or more; and (f) a step of collecting the parvovirus-containing culture supernatant obtained by culturing in the step (e);

wherein in the step (b), when A satisfying the equation (1) is absent, the steps (a) and (b) are performed again by using another cell density A when infecting virus.

[2] The method described in [1], wherein the host cells are adhesion-dependent cells.

[3] The method described in [1] or [2], wherein the parvovirus is porcine parvovirus (PPV), canine parvovirus (CPV), minute virus of mice (MVM), rat virus (RV), H-1 virus (H-1), feline parvovirus (FPV), goose parvovirus (GPV), or bovine parvovirus (BPV).

[4] The method described in any of [1] to [3], wherein the step (e) is a step of replacing the culture supernatant with a serum-free medium and culturing for 24 hours or more.

[5] The method described in any of [1] to [4], wherein the step (b) includes a step of calculating $B_{max}$ and A1' which is A that satisfies the following equation (1'):

$$B_{max}/A_{1'} \geq 2.0 \quad \text{Equation (1').}$$

[6] The method of producing a parvovirus described in any of [1] to [5], wherein culturing in the steps (d) and (e) are performed at a temperature of 33° C. or more to 39° C. or less.

[7] The method of producing a parvovirus described in any of [1] to [6], wherein in the steps (d) and (e), the host cells and the parvovirus grow concurrently.

[8] The method described in any of [1] to [7], wherein the step (f) includes a step of removing free host cells and host cell debris contained in the culture supernatant.

[9] The method described in [8], wherein the removing step is performed using filtration through a membrane having a pore size of from 0.2 μm to 0.45 μm.

[10] A parvovirus having an infectivity titer of $10^9$ $TCID_{50}$/mL or more, obtained by the method described in any of [1] to [9].

[11] A parvovirus derived from an unconcentrated cell culture supernatant, having an infectivity titer of $10^9$ $TCID_{50}$/mL or more and having a {(infectivity titer of the parvovirus ($TCID_{50}$/mL)}:{impurity protein concentration (ng/mL)} ratio more than 5000:1.

Advantageous Effects of Invention

According to the present invention, a high-infectivity-titer and high-purity parvovirus can be obtained conveniently and efficiently by cell culture. This makes it possible to eliminate harmful effects due to less infectivity titer and presence of an impurity protein during the use of the parvovirus.

DESCRIPTION OF EMBODIMENTS

The embodiment of the present invention (which will hereinafter be called "the present embodiment") will hereinafter be described in detail. The present invention is however not limited to or by the following embodiment and can be modified in various ways within the scope of the invention.

The present embodiment relates to a method of producing a parvovirus having an infectivity titer as high as $10^9$ $TCID_{50}$/mL or more and having a virus infectivity titer of 5000 ($TCID_{50}$/mL)/(ng/mL) or more relative to the impurity protein concentration thus having a high purity, including:

(a) a step of preliminarily calculating, every 24 hours, a time-dependent change of a cell density in a culture substrate when host cells are infected with a parvovirus for each cell density (A) when infecting virus;

(b) a step of determining, based on the time-dependent change of a cell density calculated preliminarily in the step (a), (b1) time ($T_{max}$) from infection to peak time of the time-dependent change of a cell density, (b2) a cell density ($B_{max}$) at $T_{max}$ and $A_1$ which is A that satisfies the following equation (1), (b3) the maximum ($A_{max}$) of the density $A_1$ when infecting virus, and (b4) $A_2$ that satisfies the following equation (2), $$B_{max}/A_1>1.2 \quad \text{Equation (1)}$$

$$A_{max} \geq A_2 \geq A_{max}/10 \quad \text{Equation (2)}$$

(c) a step of inoculating a seed virus of a parvovirus into the culture substrate containing host cells having the cell density $A_2$ when infecting virus determined in (b4) of the step (b) and a serum medium to give a multiplicity of infection (MOI) of from 0.001 to 0.1;

(d) a step of culturing a cultured product containing the host cells and the parvovirus obtained in the step (c) for a time period of $T_{max}$ or more to less than ($T_{max}$+48) hours, wherein $T_{max}$ is determined in (b1) of the step (b);

(e) a step of replacing a culture supernatant obtained in the step (d) with a serum-free medium and culturing for 12 hours or more; and (f) a step of collecting the parvovirus-containing culture supernatant obtained by culturing in the step (e);

wherein in the step (b), when A satisfying the equation (1) is absent, the steps (a) and (b) are performed again by using another cell density A when infecting virus.

Step (a): First, a time-dependent change of a cell density in a culture substrate at the time when parvovirus host cells are infected with a parvovirus is calculated preliminarily every 24 hours for each cell density (A) when infecting virus. The host cells can be grown by subculture.

A parvovirus is a small linear single-stranded DNA virus. A DNA virus is a virus having DNA as a genome. It synthesizes mRNA from the genome DNA by making use of the RNA polymerase of a host cell, synthesizes a protein based on the mRNA, and grows. Most of DNA viruses are double-stranded ones, but a parvovirus has linear single-stranded DNA as a genome. Since a virus cannot grow when it is a single-stranded DNA, a parvovirus has a unique growth mechanism in which it becomes double-stranded DNA using both the RNA polymerase of a host cell and DNA polymerase and then grows.

As viruses belonging to the Parvoviridae family, known are: three genera belonging to Parvovirinae, that is, the genus Parvorivirus which does not need a helper virus for virus replication and grows autonomously in a host cell, the genus Dependovirus which needs a helper virus, and the genus Erythrovirus which infects erythrocyte-specifically; and three genera belonging to Densovirinae, that is, the genus Densovirus which infects insects, the genus *Iteravirus*, and the genus *Aedes aegypti* densovirus. In the present embodiment, the term "parvovirus" as used in the present embodiment means a virus belonging to the genus Parvorivirus. Viruses belonging to the genus Parvorivirus all have a similar growth mechanism so that the method of the present embodiment can be used in common for them.

More specifically, viruses belonging to the genus Parvorivirus have neither a helper protein for inducing DNA metabolism of cells (resting cells) which are cells whose growth is at rest nor a double-stranded transcription template so that they cannot express their own gene until the DNA synthesis mechanism of the host cell becomes active with the start of the S phase and a DNA complementary chain is provided by the host cell. Since the viruses belonging to the genus Parvorivirus cannot induce DNA metabolism of cells whose growth is at rest and therefore cannot make use of their synthesis system, they have a growth mechanism in which they infect dividing and growing cells in the S phase and grow with the growth of these cells.

The parvovirus (virus belonging to the genus Parvorivirus) in the present embodiment includes, but not limited to, porcine parvovirus (PPV), canine parvovirus (CPV), minute virus of mice (MVM), rat virus (RV), H-1 virus (H-1), feline parvovirus (FPV), goose parvovirus (GPV), and bovine parvovirus (BPV). These viruses are analogous in size, genome structure, virus particle structure, and growth mechanism and they are all suited for use in the method of the present embodiment.

In the present embodiment, the term "parvovirus" means both of a parvovirus and a parvovirus solution which is a solutions containing the parvovirus unless otherwise particularly specified. The parvovirus solution is not particularly limited insofar as it contains a parvovirus and it embraces, for example, a culture supernatant after culture of a host cell infected with a parvovirus and a virus suspension after removal of an impurity from the resulting culture supernatant.

The "host cell" in the present embodiment may be any type of cells insofar as they are cells susceptible to the above-described parvovirus (cells which can be infected with the parvovirus). Examples of the cell susceptible to the parvovirus include: PK-13 cells, PK-15 cells, LCC-PK1 cells, ESK (embryonic swine kidney) cells, SK cells, ST (swine testes) cells, and MPK (Minipig kidney) cells, each susceptible to porcine parvovirus; MDCK (Mardin-Darby canine kidney) cells, FEA (feline embryonic fibroblast) cells, CRFK (Crandell feline kidney) cells, and FK-81 (embryonic feline kidney) cells, each susceptible to canine parvovirus; A9 (mouse fibroblast) cells and C6 (rat glial) cells, each susceptible to minute virus of mice; NRK (normal rat kidney) cells susceptible to rat virus; Molt-4 (human T-cells) cells, AV-1 (human B-cells) cells, and NC-37 (human B-cells) cells, each susceptible to H-1 virus; CRFK cells, Mya 1 cells, NLFK (Norden Laboratories Feline Kidney) cells, and A72 cells, each susceptible to feline parvovirus; GEF (goose embryo fibroblast) cells susceptible to goose parvovirus; and BEK (bovine embryonic kidney) cells, buffalo lung fibroblast cells, and EBTr (bovine embryonic trachea) cells, each susceptible to bovine parvovirus. As the host cell, a cell causing cell degeneration by infection can be preferably used. For example, porcine kidney cells can be used for porcine parvovirus and canine kidney cells can be used for canine parvovirus. A host cell is not limited to them and as described above, cells can be widely used as a host cell insofar as they are cells susceptible to a parvovirus, preferably cells causing cell degeneration. In the present embodiment, as the "host cell", animal cells having infinite growth capacity can be used and those generally called "cell line" can be used.

In the present embodiment, the host cell is preferably an adhesion-dependent cell from the viewpoint of easy medium replacement. The "adhesion-dependent cell" is a cell, like a muscle cell or organ cell, which cannot survive or grow without adhering to a culture substratum. The adhesion-dependent cell is cultured after causing it to adhere to the bottom surface or wall surface of a culture substrate such as a culture flask or a carrier called a microcarrier. A flask or a petri dish is generally used for small-scale culture. The culture using a microcarrier has an advantage that it can be easily scaled up successively (Japanese Patent No. 3982843, Successive culturing method of animal cells using porous carrier). In the present embodiment, a floating cell can also be used. The "floating cell" grows in a floating state and is cultured by allowing it to stand or stirring it while being suspended in a medium. The floating cell is desirably cultured while being attached to, for example, a microcarrier because of difficulty in medium replacement before collection of the culture supernatant.

In the present embodiment, a "culture substrate" is not limited in the kind and the term embraces any culture substrate ordinarily used in cell culture such as culture vessel, culture flask, petri dish, roller bottle, or culture plate.

The culture can be performed in an environment of an about 5% carbon dioxide gas on a medium used ordinarily in a technical field such as Dulbecco's Modified Eagle medium (DMEM medium), an Eagle medium (MEM medium) or a F-12 medium, preferably on a Dulbecco's Modified Eagle medium (DMEM medium). The environment and culture conditions are not limited to them insofar as they are suited for the growth of the host cell. The culture temperature may be a temperature suited for the growth of host cells. Host cells for parvovirus are known to grow within a range of from 33° C. to 39° C. ("Introduction to Animal Cell Culturing Method (Biochemical Experimental Method 29), by Yutaka Matsutani/Gakkai Shuppan Center" p. 14-15) so that the culture temperature can be set preferably at 33° C. or higher and 39° C. or lower, for example, at about 37° C. Use of a medium containing 10% or less of an animal serum (such as fetal bovine serum, calf serum, or horse serum) containing a cell growth factor is desired and use of a medium same as that used in the steps (c) and (d) described later is preferred.

In the present embodiment, the "infectivity titer" is a unit expressing the infectious titer of a virus. It has the same meaning as "Titer" often used in the virus industry. A virus cannot be seen even using an optical microscope so that different from biological cells, density (the number of virus particles/volume) of the virus cannot be measured under the microscope. An infectious titer making use of infectious ability to host cells as a unit is used as an alternative of the amount or concentration of the virus. For example, when a virus suspension obtained by diluting a single layer of host cells at an appropriate ratio is added, the number of the virus is detected as a plaque and an infectious titer can be measured as a plaque forming unit (pfu)/mL. Alternatively, an infectious titer can be measured as 50% tissue culture infectious dose ($TCID_{50}$)/mL, which is a concentration at which infection is positive in 50% of host cells measured upon continuous dilution of a liquid containing a virus. In the present embodiment, the infectious titer of the parvovirus used can be measured as $TCID_{50}$/mL and the infectious titer can be expressed as $TCID_{50}$/mL. The infectious titer of the parvovirus may be expressed by another unit such as pfu/mL. In the parvovirus whose infectious titer can be measured by another unit, conversion between different units can be achieved easily by measuring the infectious titer of the same parvovirus suspensions by these two units simultaneously.

In the present embodiment, calculating, "every 24 hours, a time-dependent change of a cell density in a culture substrate when host cells are infected with a parvovirus" can be performed by inoculating host cells, which are infected with a parvovirus at a predetermined multiplicity of infection (MOI), in a culture vessel, collecting the resulting cells every 24 hours, and then counting the number of the cells in the culture substrate. The term "multiplicity of infection" as used herein means a ratio of the addition amount of a virus to the number of host cells and is expressed by (infection titer of virus)/(number of host cells). After the host cells are infected with a parvovirus, the cells first grow and the cell density in the culture substrate increases. After an elapse of a predetermined time, the cells are sensitized with the virus and start dying so that the cell density decreases after it reaches a peak. Such a time-dependent change is calculated for each of the cultures classified according to the number of host cells when infecting parvovirus.

The number of cells can be counted by a method known to those skilled in the art, for example, as follows. First, a small amount of a protease such as trypsin or a chelating agent such as EDTA, or a mixture thereof is added to cells that have adhered to a cell substrate to release host cells from a culture vessel. After the cell solution thus released is diluted with a serum-containing medium to suppress cell releasing action, the diluted solution is poured in a hemocytometer or the like and the number of cells is counted under a microscope. Alternatively, the number of cells can be counted using a cell sorter or cell counter.

In the step (a) of the present embodiment, a time-dependent change of the cell density after infection is calculated every 24 hours for each of respectively different cell densities (A) when infecting virus. A method of selecting the cell number when infecting virus in the step (a) is not particularly limited insofar as A that satisfies the equation (1) can be selected in the step (b) which will be described later. When there is no A that satisfies the equation (1) in the step (b), the steps (a) and (b) can be performed again with another A.

In one aspect, with the cell density of host cells in a confluent state (this cell density will hereinafter be called "C") as a standard, from about C to C/100, for example, about C, C/3, C/10, C/30, and C/100 can be selected as A.

Step (b): An appropriate cell density when infecting virus is determined based on the time-dependent change of the cell density calculated in advance in the step (a).

(b1) The host cells infected with a parvovirus grow during a certain time after infection, but after their growth reaches its peak, they die due to sensitization with the virus so that first, time from infection until the peak time of the time-dependent change of the cell density ($T_{max}$) is determined.

(b2) Next, a cell density at $T_{max}$ ($B_{max}$) and $A_1$ which is A that satisfies the following equation (1) are determined.

$$B_{max}/A_1>1.2 \quad \text{Equation (1)}$$

In the growth mechanism peculiar to parvovirus, virus and host cells grow simultaneously so that an appropriate cell number $A_1$ when infecting virus is presumed to be such that the number of cells at the peak time $T_{max}$ becomes more than 1.2 times, for example, 1.5 times or more, preferably 1.75 times or more, more preferably 2.0 times or more, compared to the cell number (A) when infecting virus. Although not bound to a theory, when A is too large, it is presumed that host cells themselves cannot grow because the number of cells is close to the number of cells under a confluent state and as a result, $B_{max}/A_1$ tends to decrease, leading to a reduction in the production amount of the virus per cell.

(b3) Next, the maximum ($A_{max}$) of the cell density $A_1$ when infecting virus is determined.

(b4) $A_2$ that satisfies the following equation (2) is determined based on the resulting $A_{max}$.

$$A_{max}\geq A2\geq A_{max}/10 \quad \text{Equation (2)}$$

When A is too small, the peak-time cell density ($B_{max}$) is not limited by the culture substrate so that $B_{max}/A_1$ is kept at a high value and the production amount of the virus per cell reaches its limit. On the other hand, the virus concentration depends on the number of the host cells so that it is presumed that as A becomes smaller, the concentration of the virus tends to be lower.

In the step (a), some As are selected and the appropriate cell number A when infecting virus is presumed to be the maximum A ($A_{max}$) of $A_1$ which is A in the case where $B_{max}/A$ satisfies the equation (1). Further, a high-infectivity-titer and high-purity parvovirus can be collected even by decreasing the cell density when infecting virus by about 1/10 of $A_{max}$. Although not bound to a theory, it is presumed that even if some reduction of A from $A_{max}$ occurs, the production amount of the virus per cell increases with the reduction of A so that the concentration of the parvovirus finally available remains unchanged.

Step (c): Next, a seed virus of the parvovirus is inoculated into the culture substrate containing the host cells having an appropriate cell density of $A_2$ determined in the step (b) and a serum medium to give a MOI of from 0.001 to 0.1.

In the step (c), a culture substrate containing the host cells having an appropriate cell density can be prepared by; inoculating the host cells into a culture substrate at a cell density smaller than $A_2$ in advance and culturing for a predetermined time to increase the cell density to $A_2$; or inoculating a host cell-containing serum medium in an amount to give the cell density of $A_2$ into a culture substrate. As the serum medium, a Dulbecco's Modified Eagle medium (DMEM medium), an Eagle medium (MEM medium), a F-12 medium, or the like containing, for example, from 0.5% to 15%, preferably from 1% to 10% of an animal serum such as fetal bovine serum, calf serum, or horse serum, may be used.

An important characteristic of the present embodiment is that the cell number when infecting virus is determined not based on the doubling time of the host cells uninfected with a virus or a parameter of them under a confluent state but based on the time dependent change of the cell density of the host cells infected with the parvovirus as described above. When a method of infecting host cells under a confluent state with a virus is performed according to a common knowledge of a conventional virus production method, growth of the host cells infected with the parvovirus is not observed. The host cells degenerate due to infection and continue to die. In the present embodiment, on the other hand, the present inventors have successfully obtained high-infectivity-titer and high-purity parvovirus by conducting infection with the parvovirus at a density of host cells which has plenty of space left for the host cells to grow at a certain ratio or more, even after infection with the virus. Although as a past finding, there is a technique of starting infection at a markedly low cell density and allowing growth of host cells and growth of a parvovirus to proceed concurrently (WO2014/080676), but a parvovirus having a higher infectivity titer and a higher purity than that obtained by the above technique can be obtained by the present embodiment.

Next, in the step (c), a seed virus of the parvovirus is inoculated into the culture substrate containing the host cells prepared as described above and having a cell density of A2 to give a multiplicity of infection (MOI) of from 0.001 to 0.1. The inoculation of a seed virus of the parvovirus may be performed to give an MOI of from 0.001 to 0.1 simultaneously with the inoculation of the host cells into the culture substrate. Alternatively, the culture of host cells may be started at a lower cell density and when the cell density reaches the above-described cell density of $A_2$, the seed virus may be inoculated to give an MOI of from 0.001 to 0.1. The above-described predetermined range of MOI is a range of a value generally used during growth of the parvovirus and values within this range do not adversely affect the object of collecting a high-concentration and high-purity virus.

Step (d): After inoculation of the seed virus of parvovirus, the cultured product containing the parvovirus and the host cells is cultured for a predetermined time. In the step (d), growth of the host cells and the parvovirus proceeds simultaneously. The culture time is, as determined in the (b1) of the step (b), ($T_{max}$), which is from infection with the virus to the peak time of the time-dependent change of the cell density, or more to less than ($T_{max}$+48) hours, for example, $T_{max}$ or more to ($T_{max}$+36) hours or less, preferably from $T_{max}$ or more to ($T_{max}$+30) hours or less, more preferably $T_{max}$ or more to ($T_{max}$+24 hours) or less. During culturing for the predetermined time, most of the seed viruses with which the host cells are infected borrow the function of the host cells, duplicate themselves in the host cells and remain in the cells.

Step (e): The culture supernatant obtained by culturing for the predetermined time in the step (d) contains a large amount of impurity proteins derived from the serum, but many of the host cells infected with the virus still continue to adhere to the culture substrate. In the present embodiment, the impurity proteins can be removed and a high-purity parvovirus can be collected by replacing the serum medium used for culture with a serum-free medium. As the serum-free medium, the medium described in the step (c) but not containing a serum can be used.

After medium replacement, by culturing for 12 hours or more, preferably 18 hours or more, more preferably 24 hours or more, the virus is released from the host cells infected with the virus and a supernatant containing the virus can be obtained. Culturing for 36 hours or more after medium replacement is presumed to have no effect on the infectivity titer of the parvovirus thus obtained. Therefore, from the viewpoint of a culturing cost, the culture time after medium replacement is set at preferably 36 hours or less.

The culture temperature at the time of culturing in the steps (d) and (e) may be set to a temperature suited for the growth of the host cells, preferably 33° C. or more and 39° C. or less, for example, about 37° C. Preferably, the culture is carried out under the conditions similar to the culture conditions in the step (a). Therefore, the culture temperature is desirably set at a temperature comparable to that when the cell density of the host cells infected with the parvovirus is calculated in advance in the step (a).

Step (f): After culturing for the predetermined time, the culture supernatant containing the parvovirus is collected. In the conventional method, infected host cells are destroyed by repeating freezing and thawing of the infected host cells to collect the virus. In this method, however, a large amount of the impurities in the host cells is released at the time of destruction. In the method of collecting the culture supernatant as in the present embodiment, although mixing of impurities derived from host cells destroyed by the virus infection is inevitable, an amount of the impurities is extremely smaller than that when the host cells are destroyed by freezing and thawing. In addition, replacement of the culture supernatant of the parvovirus and host cells with a serum-free medium considerably decreases the amount of impurities derived from the serum compared with culture using only a serum medium. In the present embodiment, therefore, a high-infectivity-titer and high-purity parvovirus can be collected easily from the culture supernatant.

By the above-described method of the present embodiment, a parvovirus having an infectivity titer as high as $10^9$ $TCID_{50}$/mL or more can be obtained.

The collection in the step (f) may include a step of removing impurities such as free host cells or host cell debris. This removal step can be achieved by low-speed centrifugal separation under known conditions. Alternatively or in addition, the impurities can be removed by filtering through a membrane having a pore size of from 0.1 to 0.5 μm, preferably from 0.2 to 0.45 μm.

The collection in the step (f) can be performed preferably without concentrating the culture supernatant. Concentration of the impurities due to the concentration step which will be described later therefore does not occur and a high-purity parvovirus can be obtained easily.

As described above, by carrying out culture and collection of parvovirus, a high-purity parvovirus having an {infectivity titer of the parvovirus ($TCID_{50}$/mL)}:{impurity protein concentration (ng/mL)} ratio more than 5000:1, preferably more than 9000:1 can be obtained. Examples of the "impurities" include free host cells or host cell debris, and proteins derived from the host cells or serum component. The free host cells or host cell debris has a large size and can be removed easily by a known method such as the above-described centrifugal separation or filtration so that in one aspect of the present embodiment, a protein concentration is used as an index showing the ratio of impurities present in the virus.

The impurity protein concentration can be measured using a method known to those skilled in the art, for example, as shown below in Examples, by the BCA method using a commercially available protein assay reagent or the like.

The present embodiment also relates to a high-purity and high-infectivity-titer parvovirus derived from an un-concentrated cell culture supernatant.

In the present embodiment, the term "concentration" means an increase in virus concentration after concentration compared with that before concentration, that is, an increase in infectivity titer. In one aspect, the parvovirus of the present embodiment is a high-purity parvovirus obtained from the culture supernatant without such a concentration and therefore having no concentrated impurity due to concentration.

Specific examples of the concentration operation include: density gradient centrifugation such as cesium density-gradient ultracentrifugation, sucrose density-gradient ultracentrifugation; ultracentrifugal separation; cation exchange column chromatography; ultrafiltration; tangential flow filtration; chemically induced precipitation; virus adsorption type chromatography; polymer induced aggregation; and membrane adsorption.

Operations other than concentration operation include centrifugal separation (centrifugal separation at 10,000×g or less and 100,000×g·h or less) other than ultracentrifugal separation and filtration through a disinfecting membrane. More specific examples include a purification operation described later in Examples.

As described above, a parvovirus having a low impurity protein concentration and therefore having a high-purity and having an infectivity titer as high as $10^9$ $TCID_{50}$/mL or more can be obtained according to the present embodiment, making it possible to overcome various negative effects which will otherwise occur due to an insufficient infectivity titer at the time of using the parvovirus. Three typical uses of the virus will hereinafter be described.

When the virus is used for the first use, that is, for research applications such as search for antiviral agents, the presence of impurities may have an adverse effect such as inhibition of an intended reaction. It is therefore necessary to produce a virus having an infectivity titer higher than that of a virus actually provided for a test in advance and provide it for the research after diluting it to avoid the influence of the impurities. To allow measurement of high virus inhibition activity, the virus should be provided at a high infectivity titer for the test so that a virus having an infectivity titer higher than that is required. This means that the virus available by cell culture is desirably higher. According to the present embodiment, a parvovirus having an infectivity titer as high as $10^9$ $TCID_{50}$/mL or more can be obtained. This makes it possible to provide it, in the research of antiviral agents using a parvovirus, as a research material after dilution and thereby makes it possible to reduce an unexpected reaction or interference due to the impurities.

For the second use, that is, for evaluating virus clearance of a biologics production process, the virus produced desirably has a high purity and high infectivity titer. As described above, what is required in this virus clearance test is firstly that the addition amount of a virus suspension is adjusted so as not to clog the filter, and secondly, that a virus suspension is added in an amount to give a log reduction value (LRV), which is a virus clearance value of a step to be evaluated, of 4 or more. For LRV to be 4 or more, the virus must be added to an intermediate product (a product to be provided for a virus removal filter step) in an amount to give a virus infectivity titer of $10^4$ $TCID_{50}$/mL. In consideration of the quantitative error in the virus infectivity titer, loss in the prefilter for removing aggregates of virus particles, and a possibility of increasing the detection lower limit of the virus (when the filter solution has cytotoxicity, a virus detection lower limit increases because the virus infectivity titer must be measured after diluting the filtered solution), it is necessary to add the virus to give an infective titer of $10^6$ $TCID_{50}$/mL or more. In order to achieve $10^6$ $TCID_{50}$/mL or more by adding 0.1% by volume of the virus suspension, the infectivity titer of the original virus suspension is required to be $10^9$ $TCID_{50}$/mL or more. A parvovirus having a high purity and having an infectivity titer as high as $10^9$ $TCID_{50}$/mL or more can be obtained according to the present embodiment so that it becomes possible to reduce the addition amount of the parvovirus considerably and overcome the problem of clogging of a filter with impurities derived from the parvovirus. As described above, as a new evaluation standard of a virus removal filter, a virus removing property when a virus loading amount per unit membrane area is made greater than the conventional amount, for example, a virus removing property when $10^{13}$ $TCID_{50}/m^2$ or more of the virus is loaded has recently attracted attentions. A virus having an infectivity titer of $10^8$ $TCID_{50}$/mL and collectable by the conventional method could be loaded only by filtering 1 L of a solution containing 1% by volume of the virus through a filter of 0.001 $m^2$ (W2014/080676). A parvovirus having a high purity and an infectivity titer as high as $10^9$ $TCID_{50}$/mL or more can be obtained according to the present embodiment so that this enables a virus loading amount of $10^{13}$ $TCID_{50}/m^2$ or more under filtering conditions same as those described above.

Also for vaccine production, which is the third use, a high-purity and a high-infectivity-titer virus produced by cell culture is advantageous in the production because the burden on a virus vaccine purification step conducted subsequently can be reduced. A virus having a low purity makes the purification step burdensome and a virus having a low virus infectivity titer makes the purification step burdensome because of a relative increase in the impurity concentration. Such a virus is therefore disadvantageous in the production. A parvovirus having a high purity and an infectivity titer as high as $10^9$ $TCID_{50}$/mL or more can be obtained according to the present embodiment so that also in the production of a parvovirus vaccine, the amount of the vaccine in a raw material to be purified increases drastically, making it possible to carry out the vaccine purification step more efficiently at a lower cost.

EXAMPLES

The present invention will hereinafter be described in further detail based on Examples and Comparative Examples. Examples shown here are typical ones and the present invention is not limited to or by them.

Example 1: Time-Dependent Change of Cell Density after Parvovirus Infection [1]

As host cells for porcine parvovirus (PPV), PK-15 cells (purchased from ATCC, Catalog No. CCL-33, parvovirus-sensitive adhesion dependent cells) were used. They were subcultured on a medium obtained by adding 10% fetal bovine serum to a Dulbecco's Modified Eagle medium (DMEM medium, product of Life Technologies, Production No. 11965-092) (which medium thus obtained will hereinafter be called "serum medium" and this will equally apply to Examples described below) in a flask for tissue culture having a base area of 75 $cm^2$ and a volume of 15 mL (which flask will hereinafter be called "flask" and this will equally apply to Examples described below) in an environment of 37° C. and 5% $CO_2$.

Then, the PK-15 cells were released from the flask and host cells having cell densities (A) of $1.8\times10^7$ cells/flask (Sample 1a), $6.0\times10^6$ cells/flask (Sample 1b), $3.0\times10^6$ cells/flask (Sample 1c), $1.2\times10^6$ cells/flask (Sample 1d), $6.0\times10^5$ cells/flask (Sample 1e), and $1.0\times10^5$ cells/flask (Sample 1f) were dispensed together with 10 mL of the serum medium in new flasks, respectively. These cell densities A when infecting virus are presumed to be C/1.67, C/5, C/10, C/25, C/50, and C/300, respectively supposing that the cell density (C) of the PK-15 cells at confluent growth is $3.0\times10^7$ cells/flask.

The cells having each cell density condition were dispensed in 3 flasks. Then, PPV was inoculated into each of the flasks to give an MOI of 0.01 and they were cultured in an environment of 37° C. and 5% $CO_2$. The cells on the bottom surface of the flask were collected at the time when they were cultured for 24 hours, 48 hours, and 72 hours after infection was started and a cell density (B) was calculated.

The number of the cells was calculated in the following manner. First, a small amount of a protease such as trypsin or a chelating agent such as EDTA, or a mixture thereof was added to the cells that had adhered to the cell substrate to release the host cells from the culture vessel. After the cell solution thus released was diluted with a serum-containing medium to suppress the cell detachment activity, the diluted solution was poured in a hemocytometer or the like and the number of cells was counted under a microscope.

The cell density at the time of virus infection (A=the number of cells/flask) and a ratio determined from this A and the cell density measured every 24 hours of culturing (B=the number of cells/flask) (B/A) are shown in Table 1. Cells are usually dying with the passage of time when infected with a virus, but the cells infected with the parvovirus continue to grow. In any cell density A when infecting virus, the total number of cells showed an increase until the elapsed time is 48 hours. When the elapsed time is 72 hours, however, the cells sensitized with the virus died and the total number of cells showed a marked decrease.

Within the range of the A in the test, as the cell density when infecting virus was higher, the cell growth rate after infection tends to decrease. But, it was not the case that the lower the cell density when infecting virus, the higher the cell growth rate after infection.

TABLE 1

A ratio (B/A) of {Cell density of parvovirus-infected cells after culture (B = cells/flask)} to: { cell density when infecting virus (A = cells/flask)}

| Elapsed | Cell density when infecting virus (A = cells/flask) | | | | | |
|---|---|---|---|---|---|---|
| time after infection (hours) | Sample 1a $1.8\times10^7$ | Sample 1b $6.0\times10^6$ | Sample 1c $3.0\times10^6$ | Sample 1d $1.2\times10^6$ | Sample 1e $6.0\times10^5$ | Sample 1f $1.0\times10^5$ |
| 0 | 1 | 1 | 1 | 1 | 1 | 1 |
| 24 | 1.13 | 1.75 | 2.30 | 2.04 | 2.43 | 1.98 |
| 48 | 1.20 | 2.10 | 2.84 | 3.60 | 3.47 | 3.50 |
| 72 | 0.14 | 0.42 | 0.52 | 0.02 | 0.67 | 0.03 |

Example 2: Medium Replacement after Culture of Parvovirus-Infected Cells [1]

In a manner similar to that of Example 1, PK-15 cells were subcultured. The host cells having cell densities similar to those of Samples 1a to 1f, respectively, were each dispensed together with 10 mL of the serum medium into 6 flasks according to the respective cell density conditions (Samples 2a to 2f). Then, PPV was inoculated into each of the flasks to give an MOI of 0.01, followed by culturing in an environment of 37° C. and 5% $CO_2$. The culture supernatant was removed from each of the flasks at the time when culture was performed for 48 hours and 72 hours after the infection was started and the cells on the bottom surface of the flask were washed with a serum-free DMEM medium (which will hereinafter be called "serum-free medium"). After addition of 10 mL of the serum-free medium, culture was performed further and the culture supernatant of the serum-free medium was collected from each of the flasks 24 hours, 48 hours, and 72 hour later. The serum-free culture supernatant thus collected was centrifuged at 3000 rpm for 20 minutes and a supernatant fraction was filtered through a 0.45 μm filter ("Millex-HV", product of Millipore).

The PPV infectivity titer was measured using a 96-well plate by a CPE-based $TCID_{50}$ method making use of cell degeneration. The 50% infectivity titer was calculated by the Reed-Muench method (Medical Virology, 2000, Nankodo Co., Ltd., p. 171-172). The results are shown in Table 2.

With regards to the numerical values shown in Table 2, the infectivity titer is expressed as a logarithm value. For example, the infectivity titer of 9.1 means $10^{9.1}$ $TCID_{50}$/mL. As shown in Table 2, the infectivity titer of the virus thus obtained in Samples 2b to 2e is as high as $10^9$ $TCID_{50}$/mL or more, while that in Samples 2a and 2f, it is less than $10^9$ $TCID_{50}$/mL under any condition.

TABLE 2

PPV Titer in culture supernatant of parvovirus-infected cells when culture time before and after medium replacement is changed (unit: log[$TCID_{50}$/mL])

| Culture time before medium replacement (hours) | Culture time after medium replacement (hours) | Cell density when infecting virus (cells/flask) Sample 2a $1.8 \times 10^7$ | Sample 2b $6.0 \times 10^6$ | Sample 2c $3.0 \times 10^6$ | Sample 2d $1.2 \times 10^6$ | Sample 2e $6.0 \times 10^5$ | Sample 2f $1.0 \times 10^5$ |
|---|---|---|---|---|---|---|---|
| 48 | 24 | 8.9 | 9.2 | 9.6 | 9.1 | 9.1 | 8.1 |
| | 48 | 8.5 | 9.1 | 9.4 | 9.4 | 9.1 | 7.9 |
| | 72 | 8.2 | 9.3 | 9.2 | 9.1 | 9.2 | 8.2 |
| 72 | 24 | 8.6 | 9.6 | 9.0 | 9.3 | 9.1 | 8.3 |
| | 48 | 8.7 | 9.3 | 9.3 | 9.6 | 9.4 | 8.1 |
| | 72 | 8.6 | 9.0 | 9.5 | 9.2 | 9.3 | 8.0 |

In addition, the impurity protein concentration was measured using a protein assay reagent (BCA method) of Thermo Scientific and a ratio of the PPV infectivity titer ($TCID_{50}$/mL) to the impurity protein concentration (ng/mL) was determined. The results are shown in Table 3. As shown in Table 3, a high-purity parvovirus having a markedly low impurity protein ratio is obtained in Samples 2b to 2e. In Samples 2a and 2f, on the other hand, the impurity protein ratio in the parvovirus thus obtained is high compared with that in Samples 2b to 2e.

TABLE 3

{PPV titer in culture supernatant of parvovirus-infected cells (unit: log[$TCID_{50}$/mL])}: { impurity protein (ng/mL)} ratio when culture time before and after medium replacement is changed

| Culture time before medium replacement (hours) | Culture time after medium replacement (hours) | Cell density when infecting virus (cells/flask) Sample 2a $1.8 \times 10^7$ | Sample 2b $6.0 \times 10^6$ | Sample 2c $3.0 \times 10^6$ | Sample 2d $1.2 \times 10^6$ | Sample 2e $6.0 \times 10^5$ | Sample 2f $1.0 \times 10^5$ |
|---|---|---|---|---|---|---|---|
| 48 | 24 | 30000:1 | 22000:1 | 28000:1 | 24000:1 | 22000:1 | 5300:1 |
| | 48 | 3100:1 | 13000:1 | 20000:1 | 22000:1 | 15000:1 | 3700:1 |
| | 72 | 1200:1 | 23000:1 | 10000:1 | 12000:1 | 22000:1 | 6800:1 |
| 72 | 24 | 4100:1 | 32000:1 | 9000:1 | 23000:1 | 22000:1 | 3400:1 |
| | 48 | 5100:1 | 28000:1 | 23000:1 | 30000:1 | 23000:1 | 3000:1 |
| | 72 | 3700:1 | 14000:1 | 40000:1 | 12000:1 | 20000:1 | 4500:1 |

The culture conditions for obtaining a high-infectivity-titer and high-purity parvovirus were determined based on the above-described results of Example 1 and Example 2.

First, based on Example 1, the time-dependent change of the cell density after infection was recorded every 24 hours for each of the cell densities (A) when infecting virus; the cell density ($B_{max}$) at the peak time ($T_{max}$=48 hours in the present example) corresponding to each of the cell densities when infecting virus was recorded, and a $B_{max}$/A ratio serving as an indicator of the cell growth rate after infection was calculated. It was considered that adoption of the cell density when infecting virus at which the $B_{max}$/A becomes at least 1.2 or more (for example, 1.5 or more, preferably 1.75 or more, more preferably 2.0 or more) enables production of a high-infectivity-titer and high-purity parvovirus. In other words, it was considered to be important that $A_1$ and $B_{max}$ satisfies the following equation (1) in order to obtain a high-infectivity-titer and high-purity parvovirus.

$$B_{max}/A1>1.2 \qquad \text{Equation (1)}$$

In addition, it was considered that a high-infectivity-titer and high-purity parvovirus can be obtained when the cell density when infecting virus is the maximum ($A_{max}$) among the cell density when infecting virus at which $B_{max}$/A becomes at least 1.2 or more. Further, it was considered that even when the above-described density is decreased by about 1/10, the virus production amount per cell increases due to a decrease in the A so that the parvovirus concentration finally obtained does not change and a high-infectivity-titer and high-purity parvovirus can be collected. In other words, it was considered to be important, in order to obtain a high-infectivity-titer and high-purity parvovirus, that the cell density when infecting virus of the host cells satisfies the following equation (2):

$$A_{max} \geq A2 \geq A_{max}/10 \qquad \text{Equation (2)}$$

Based on Example 2, it was considered that a high-infectivity-titer and high-purity parvovirus can be obtained by adopting the cell density when infecting virus within the above-described range, replacing the culture supernatant with the serum-free medium at the time when the time-dependent change of the cell density reaches a peak or after passage of a predetermined time from the peak time, and culturing for a predetermined time, for example, 12 hours or more, preferably 18 hours or more, more preferably 24 hours or more.

Comparative Example 1

In a manner similar to that of Example 1, PK-15 cells were subcultured. The host cells having cell densities similar to those of Samples 1b to 1e, respectively, were each dispensed together with 10 mL of the serum medium into 3 flasks according to the respective cell density conditions (Samples 3b to 3e). Then, PPV was inoculated into each of the flasks to give an MOI of 0.01, followed by culturing in an environment of 37° C. and 5% $CO_2$. The culture supernatant was removed from each of the flasks at the time when culture was performed for 96 hours after the infection was started and the cells on the bottom surface of the flask were washed with a serum-free DMEM medium (which will hereinafter be called "serum-free medium"). After addition of 10 mL of the serum-free medium, culture was performed further and the culture supernatant of the serum-free medium was collected from each of the flasks 24 hours, 48 hours, and 72 hours later. The serum-free culture supernatant thus collected was centrifuged at 3000 rpm for 20 minutes (1710×g, 20 minutes=570×g·h) and a supernatant fraction was filtered through a 0.45-μm filter (product of Millipore).

The PPV infectivity titer was measured using a 96-well plate in a manner similar to that of Example 2. The results are shown in Table 4. As shown in Table 4, the respective infectivity titers of the viruses obtained in Samples 3b to 3e were low under any condition compared with Samples 2b to 2e having cell densities when infecting virus equal to those of the Samples 3b to 3e, respectively, and did not reach $10^9$ $TCID_{50}$/mL or more. It has been revealed that the culture time before the medium replacement has an influence on the infectivity titer of the virus thus obtained.

TABLE 4

PPV Titer in culture supernatant of parvovirus-infected cells when culturing is performed for 96 hours after infection and then the culture time after medium replacement is changed (unit: log[$TCID_{50}$/mL])

| Culture time before medium replacement (hours) | Culture time after medium replacement (hours) | Cell density when infecting virus (cells/flask) Sample 3b $6.0 \times 10^6$ | Sample 3c $3.0 \times 10^6$ | Sample 3d $1.2 \times 10^6$ | Sample 3e $6.0 \times 10^5$ |
|---|---|---|---|---|---|
| 96 | 24 | 8.2 | 8.5 | 7.9 | 8.0 |
| | 48 | 8.0 | 8.2 | 8.2 | 8.0 |
| | 72 | 8.0 | 8.3 | 8.3 | 8.2 |

Further, in a manner similar to that of Example 2, a ratio of the PPV infectivity titer ($TCID_{50}$/mL) to the impurity protein concentration (ng/mL) was determined. The results are shown in Table 5. The proportion of the impurity protein in the parvovirus obtained in Samples 3b to 3e was higher than that obtained in Samples 2b to 2e having cell densities when infecting virus equal to those of the Samples 3b to 3e, respectively. It has been revealed that the culture time before medium replacement had also an influence on the purity of the virus thus obtained.

It was considered from the results of Example 2 and Comparative Example 1 that a high-purity and high-infectivity-titer parvovirus can be obtained by replacement with the serum-free medium after culture is performed for less than 48 hours from the time when the time-dependent change of the cell density reaches a peak, for example, within 36 hours, preferably within 30 hours, more preferably within 24 hours.

TABLE 5

{PPV titer in culture supernatant of parvovirus-infected cells (unit: log[$TCID_{50}$/mL])}: {impurity protein (ng/mL)} ratio when culturing is performed for 96 hours after infection and then the culture time after medium replacement is changed

| Culture time before medium replacement (hours) | Culture time after medium replacement (hours) | Cell density when infecting virus (cells/flask) Sample 3b $6.0 \times 10^6$ | Sample 3c $3.0 \times 10^6$ | Sample 3d $1.2 \times 10^6$ | Sample 3e $6.0 \times 10^6$ |
|---|---|---|---|---|---|
| 96 | 24 | 3400:1 | 6500:1 | 1000:1 | 5000:1 |
| | 48 | 4000:1 | 6000:1 | 2300:1 | 1800:1 |
| | 72 | 4300:1 | 4100:1 | 4600:1 | 3300:1 |

Example 3: Time-Dependent Change of Cell Density after Infection with Parvovirus [2]

As host cells of minute virus of mice (MVM), A9 cells (purchased from ATCC, Catalog No. CCL-1.4, parvovirus-sensitive adhesion-dependent cells) were used and they were subcultured on the serum medium in a flask in an environment of 37° C. and 5% $CO_2$.

Then, the A9 cells were released from the flask and host cells having cell densities (A) of $6.0\times10^6$ cells/flask (Sample 4a), $3.0\times10^6$ cells/flask (Sample 4b), $1.5\times10^6$ cells/flask (Sample 4c), $6.0\times10^6$ cells/flask (Sample 4d), $3.0\times10^5$ cells/flask (Sample 4e), and $1.0\times10^5$ cells/flask (Sample 40 were dispensed together with 10 mL of the serum medium in new flasks, respectively. Those cell densities A when infecting virus are considered to be C/5, C/10, C/20, C/50, C/100 and C/300, respectively supposing that the cell density (C) of the A9 cells at confluent growth is set at $3.0\times10^7$ cells/flask.

The cells having respective cell density conditions were each dispensed in 3 flasks. Then, MVM was inoculated into each of the flasks to give an MOI of 0.01, followed by culturing in an environment of 37° C. and 5% $CO_2$. The cells on the bottom surface of the flask were collected at the time when the culture was performed for 72 hours, 96 hours, and 120 hours after infection was started and the cell density (B) was calculated.

The number of the cells was calculated in the following manner. First, a small amount of a protease such as trypsin or a chelating agent such as EDTA, or a mixture thereof was added to the cells that had adhered to the cell substrate and the host cells were released from the culture vessel. After the cell solution thus released was diluted with a serum-containing medium to suppress the cell detachment activity, the diluted solution was poured in a hemocytometer or the like and the number of cells was counted under a microscope.

The cell density at the time of virus infection (A=the number of cells/flask) and a ratio determined from this A and the cell density measured every 24 hours of culturing (B=the number of cells/flask) (B/A) are shown in Table 6. Cells are usually dying with the passage of time when infected with a virus, but the cells infected with the parvovirus continue to grow. In any cell density A when infecting virus, the total number of cells showed an increase until the elapsed time is 72 hours. When the elapsed time was 96 hours, however, the cells sensitized with the virus died and the total number of cells showed a decrease.

Within the range of the A tested, as the cell density when infecting virus was higher, the cell growth rate after infection tends to decrease. But, it was not the case that the lower the cell density when infecting virus, the higher the cell growth rate after infection.

TABLE 6

A ratio (B/A) of {cell density after parvovirus-infected cells are cultured (B = cells/flask)} to {cell density at the time of infection with the virus (A = cells/flask)}

| Elapsed time after infection (hours) | Cell density when infecting virus (A = cells/flask) Sample 4a $6.0 \times 10^6$ | Sample 4b $3.0 \times 10^6$ | Sample 4c $1.5 \times 10^6$ | Sample 4d $6.0 \times 10^5$ | Sample 4e $3.0 \times 10^5$ | Sample 4f $1.0 \times 10^5$ |
|---|---|---|---|---|---|---|
| 0 | 1 | 1 | 1 | 1 | 1 | 1 |
| 72 | 1.09 | 1.49 | 2.30 | 3.04 | 3.42 | 2.97 |
| 96 | 1.18 | 2.21 | 4.17 | 4.60 | 4.90 | 4.25 |
| 120 | 1.11 | 2.17 | 3.91 | 4.52 | 3.76 | 3.11 |

Example 4: Medium Replacement after Culture of Parvovirus-Infected Cells [2]

In a manner similar to that of Example 3, A9 cells were subcultured. The host cells having cell densities similar to those of Samples 4a to 4f, respectively, were each dispensed together with 10 mL of the serum medium into 6 flasks according to the respective cell density conditions (Samples 5a to 5f). Then, MVM was inoculated into each of the flasks to give an MOI of 0.01, followed by culturing in an environment of 37° C. and 5% $CO_2$. The culture supernatant was removed from each of the flasks at the time when culture was performed for 96 hours and 120 hours after the infection was started and the cells on the bottom surface of the flask were washed with the serum-free medium. After addition of 10 mL of the serum-free medium, culture was performed further and the culture supernatant of the serum-free medium was collected from each of the flasks 24 hours, 48 hours, and 72 hour later. The serum-free culture supernatant thus collected was centrifuged at 3000 rpm for 20 minutes and a supernatant fraction was filtered through a 0.45-μm filter ("Millex-HV", product of Millipore).

The MVM infectivity titer was measured in a manner similar to that of Example 2. The results are shown in Table 7. With regards to the numerical values in Table 7, the infectivity titer is expressed as a logarithm value. For example, the infectivity titer of 9.1 means $10^{9.1}$ $TCID_{50}$/mL. As shown in Table 7, the infectivity titer of the virus thus obtained in Samples 5b to 5e was as high as $10^9$ $TCID_{50}$/mL or more, while that in Samples 5a and 5f, it was less than $10^9$ $TCID_{50}$/mL under any condition.

TABLE 7

MVM Titer in culture supernatant of parvovirus-infected cells when the culture time before and after medium replacement is changed (unit: log[$TCID_{50}$/mL])

| Culture time before medium replacement (hours) | Culture time after medium replacement (hours) | Cell density when infecting virus (cells/flask) Sample 5a $6.0 \times 10^6$ | Sample 5b $3.0 \times 10^6$ | Sample 5c $1.5 \times 10^6$ | Sample 5d $6.0 \times 10^5$ | Sample 5e $3.0 \times 10^5$ | Sample 5f $1.0 \times 10^5$ |
|---|---|---|---|---|---|---|---|
| 96 | 24 | 8.2 | 9.0 | 9.2 | 9.4 | 9.1 | 7.8 |
| | 48 | 7.8 | 9.0 | 9.5 | 9.1 | 9.0 | 8.5 |
| | 72 | 7.9 | 9.3 | 9.2 | 9.0 | 9.0 | 7.5 |
| 120 | 24 | 8.5 | 9.1 | 9.3 | 9.1 | 9.2 | 8.2 |
| | 48 | 8.5 | 9.2 | 9.5 | 9.0 | 9.1 | 8.5 |
| | 72 | 8.5 | 9.2 | 9.0 | 9.5 | 9.1 | 8.0 |

In addition, the impurity protein concentration was measured using a protein assay reagent (BCA method) of Thermo Scientific and a ratio of the MVM infectivity titer ($TCID_{50}$/mL) to the impurity protein concentration (ng/mL) was determined. The results are shown in Table 8. As shown in Table 8, a high-purity parvovirus having a markedly low impurity protein ratio was obtained in Samples 5b to 5e. In Samples 5a and 5f, on the other hand, the impurity protein ratio in the parvovirus thus obtained was high compared with that in Samples 5b to 5e.

TABLE 8

{MVM titer in culture supernatant of parvovirus-infected cells (unit: log[$TCID_{50}$/mL])}: {impurity protein (ng/mL)} ratio when culture time before and after medium replacement is changed

| Culture time before medium replacement (hours) | Culture time after medium replacement (hours) | Cell density when infecting virus (cells/flask) Sample 5a $6.0 \times 10^6$ | Sample 5b $3.0 \times 10^6$ | Sample 5c $1.5 \times 10^6$ | Sample 5d $6.0 \times 10^5$ | Sample 5e $3.0 \times 10^5$ | Sample 5f $1.0 \times 10^5$ |
|---|---|---|---|---|---|---|---|
| 96 | 24 | 5300:1 | 13000:1 | 17000:1 | 31000:1 | 12000:1 | 1200:1 |
| | 48 | 1100:1 | 24000:1 | 31000:1 | 16000:1 | 35000:1 | 4600:1 |
| | 72 | 3900:1 | 16100:1 | 9400:1 | 9000:1 | 14000:1 | 1100:1 |
| 120 | 24 | 6300:1 | 22000:1 | 8900:1 | 19000:1 | 26000:1 | 5800:1 |
| | 48 | 8800:1 | 16000:1 | 26000:1 | 12000:1 | 9800:1 | 2700:1 |
| | 72 | 4500:1 | 26000:1 | 20000:1 | 34000:1 | 16000:1 | 3800:1 |

The culture conditions for obtaining a high-infectivity-titer and high-purity parvovirus were determined based on the above-described results of Example 3 and Example 4.

First, based on Example 3, the time-dependent change of the cell density after infection was recorded every 24 hours for each of the cell densities (A) when infecting virus; the cell density ($B_{max}$) at the peak time ($T_{max}$=96 hours in the present example) corresponding to each of the cell densities when infecting virus was recorded; and a $B_{max}$/A ratio serving as an indicator of the cell growth rate after infection was calculated. It was considered from the results that adoption of the cell density when infecting virus at which the $B_{max}$/A becomes at least 1.2 or more (for example, 1.5 or more, preferably 1.75 or more, more preferably 2.0 or more) enables production of a high-infectivity-titer and high-purity parvovirus. In other words, it was considered to be important that $A_1$ and $B_{max}$ satisfy the following equation (1) in order to obtain a high-infectivity-titer and high-purity parvovirus.

$$B_{max}/A1>1.2 \qquad \text{Equation (1)}$$

In addition, it was considered that a high-infectivity-titer and high-purity parvovirus can be obtained when the cell density when infecting virus is the maximum ($A_{max}$) of the cell density when infecting virus at which $B_{max}$/A becomes at least 1.2 or more. Further, it was considered that even when the above-described density is decreased by about 1/10, the virus production amount per cell increases due to a decrease in the A so that the parvovirus concentration finally obtained does not change and a high-infectivity-titer and high-purity parvovirus can be collected. In other words, it was considered to be important, in order to obtain a high-infectivity-titer and high-purity parvovirus, that the cell density when infecting virus of the host cells satisfies the following equation (2):

$$A_{max} \geq A_2 \geq A_{max}/10 \qquad \text{Equation (2)}$$

Based on Example 4, it was considered that a high-infectivity-titer and high-purity parvovirus can be obtained by adopting the cell density when infecting virus within the above-described range, replacing the culture supernatant with the serum-free medium at the time when the time-dependent change of the cell density reaches a peak or after passage of a predetermined time from the peak time, and culturing for a predetermined time, for example, 12 hours or more, preferably 18 hours or more, more preferably 24 hours or more.

Comparative Example 2

In a manner similar to that of Example 3, A9 cells were subcultured. The host cells having cell densities similar to those of Samples 4b to 4e, respectively, were each dispensed in a new flask (3 flasks for each sample) together with 10 mL of the serum medium according to the respective cell density conditions (Samples 6b to 6e). Then, MVM was inoculated into each of the flasks to give an MOI of 0.01, followed by culturing in an environment of 37° C. and 5% $CO_2$. The culture supernatant was removed from each of the flasks at the time when culture was performed for 144 hours after the infection was started and the cells on the bottom surface of the flask were washed with the serum-free medium. After addition of 10 mL of the serum-free medium, culture was performed further and the culture supernatant of the serum-free medium was collected from the flasks 24 hours, 48 hours, and 72 hours later, respectively. The serum-free culture supernatant thus collected was centrifuged at 3000 rpm for 20 minutes (1710×g, 20 minutes=570×g·h) and a supernatant fraction was filtered through a 0.45 μm filter (product of Millipore).

The MVM infectivity titer was measured using a 96-well plate in a manner similar to that of Example 2. The results are shown in Table 9. As shown in Table 9, the respective infectivity titers of the viruses obtained in Samples 6b to 6e were low under any condition compared with Samples 5b to 5e having cell densities when infecting virus equal to those of the Samples 6b to 6e, respectively, and did not reach $10^9$ $TCID_{50}$/mL or more. It has been revealed that the culture time before the medium replacement has an influence on the infectivity titer of the virus thus obtained.

TABLE 9

MVM titer in culture supernatant of parvovirus-infected cells when culturing is performed for 144 hours after infection and then culture time after medium replacement is changed (unit: log[$TCID_{50}$/mL])

| Culture time before medium replacement (hours) | Culture time after medium replacement (hours) | Cell density when infecting virus (cells/flask) Sample 6b $3.0 \times 10^6$ | Sample 6c $1.5 \times 10^6$ | Sample 6d $6.0 \times 10^6$ | Sample 6e $3.0 \times 10^5$ |
|---|---|---|---|---|---|
| 144 | 24 | 8.1 | 7.9 | 8.5 | 7.5 |
| | 48 | 7.5 | 8.0 | 8.1 | 7.5 |
| | 72 | 8.3 | 8.0 | 8.2 | 7.0 |

Further, in a manner similar to that of Example 2, a ratio of the MVM infectivity titer ($TCID_{50}$/mL) to the impurity protein concentration (ng/mL) was determined. The results are shown in Table 10. The proportion of the impurity protein in the resulting parvovirus in Samples 6b to 6e was higher than that of Samples 5b to 5e having cell densities when infecting virus equal to those of the Samples 6b to 6e, respectively. It has been revealed that the culture time before medium replacement has also an influence on the purity of the virus thus obtained.

The results of Example 4 and Comparative Example 3 have suggested that a high-purity and high-infectivity-titer parvovirus can be obtained by replacement with the serum-free medium after culture is performed for less than 48 hours from the time when the time-dependent change of the cell density reaches a peak, for example, within 36 hours, preferably within 30 hours, more preferably within 24 hours.

TABLE 10

{MVM titer in culture supernatant of parvovirus-infected cells (unit: log[$TCID_{50}$/mL])}: {impurity protein (ng/mL)} ratio when culturing is performed for 144 hours after infection and then the culture time after medium replacement is changed

| Culture time before medium replacement (hours) | Culture time after medium replacement (hours) | Cell density when infecting virus (cells/flask) Sample 6b $3.0 \times 10^6$ | Sample 6c $1.5 \times 10^6$ | Sample 6d $6.0 \times 10^5$ | Sample 6e $3.0 \times 10^5$ |
|---|---|---|---|---|---|
| 144 | 24 | 6300:1 | 3600:1 | 11000:1 | 1000:1 |
| | 48 | 2000:1 | 5000:1 | 3200:1 | 1500:1 |
| | 72 | 8900:1 | 2800:1 | 4800:1 | 3300:1 |

INDUSTRIAL APPLICABILITY

A high-purity and high-infectivity-titer parvovirus can be obtained using the method of the present invention. This parvovirus can be used for the preparation of a virus research material for searching antiviral agents, the preparation of a virus to be used for virus clearance safety evaluation in the production process of biologics (pharmaceutical product), vaccine production, or the like. The present invention has industrial applicability in these fields.

This application claims priority to Japanese Patent Application No. 2015-218775, filed on Nov. 6, 2015, the contents of which are incorporated herein by reference.

What is claimed is:

1. A method of producing a high-infectivity-titer and high-purity parvovirus, comprising:

(a) preliminarily calculating, every 24 hours, a time-dependent change of a cell density of a culture substrate when host cells are infected with a parvovirus for each cell density (A) when infecting virus;

(b) determining, based on the time-dependent change of a cell density calculated preliminarily in preliminarily calculating (a), (b1) time ($T_{max}$) from infection to peak time of the time-dependent change of a cell density, (b2) a cell density ($B_{max}$) at $T_{max}$ and $A_1$ which is A that satisfies the following equation (1), (b3) the maximum ($A_{max}$) of the cell density $A_1$ when infecting virus, and (b4) $A_2$ that satisfies the following equation (2);

$$B_{max}/A_1>1.2 \quad \text{Equation (1)}$$

$$A_{max}\geq A_2\geq A_{max}/10 \quad \text{Equation (2)}$$

(c) inoculating a seed virus of the parvovirus into the culture substrate containing host cells having the cell density $A_2$ when infecting virus determined in (b4) of the determining (b) and a serum medium to give a multiplicity of infection (MOI) of from 0.001 to 0.1;

(d) culturing a cultured product containing the host cells and the parvovirus obtained in the inoculating (c) for a time period of $T_{max}$ or more to less than ($T_{max}$+48) hours, wherein $T_{max}$ is determined in (b1) of the determining (b);

(e) replacing a culture supernatant obtained in the culturing (d) with a serum-free medium and culturing for 12 hours or more; and (f) collecting the parvovirus-containing culture supernatant obtained by culturing in the replacing (e);

wherein determination of (b1)-(b4) via the preliminarily calculating (a) and determining (b) is followed by performance of (c)-(f), and in the determining (b), when A satisfying the equation (1) is absent, the preliminarily calculating (a) and determining (b) are performed again by using another cell density A when infecting virus.

2. The method according to claim 1, wherein the host cells are adhesion-dependent cells.

3. The method according to claim 1, wherein the parvovirus is porcine parvovirus (PPV), canine parvovirus (CPV), minute virus of mice (MVM), rat virus (RV), H-1 virus (H-1), feline parvovirus (FPV), goose parvovirus (GPV), or bovine parvovirus (BPV).

4. The method according to claim 1, wherein the replacing (e) includes replacing the culture supernatant with a serum-free medium and culturing for 24 hours or more.

5. The method according to claim 1, wherein the determining (b) comprises calculating $B_{max}$ and A1' which is A that satisfies the following equation (1'):

$$B_{max}/A_{1'}\geq 2.0 \quad \text{Equation (1')}.$$

6. The method according to claim 1, wherein culturing in the culturing (d) and replacing (e) are performed at a temperature of 33° C. or more and 39° C. or less.

7. The method according to claim 1, wherein in the culturing (d) and replacing (e), the host cells and the parvovirus grow concurrently.

8. The method according to claim 1, wherein the collecting (f) comprises removing free host cells and host cell debris contained in the culture supernatant.

9. The method according to claim 8, wherein the removing is performed using filtration through a membrane having a pore size of from 0.2 μm to 0.45 μm.

* * * * *